United States Patent [19]
Lee et al.

[11] Patent Number: 5,641,504
[45] Date of Patent: Jun. 24, 1997

[54] SKIN PERMEATION ENHANCER COMPOSITIONS USING GLYCEROL MONOLINOLEATE

[75] Inventors: Eun Soo Lee, Redwood City; Diane E. Nedberge; Su Il Yum, both of Los Altos, all of Calif.

[73] Assignee: Alza Corporation, Palo Alto, Calif.

[21] Appl. No.: 162,026

[22] PCT Filed: May 20, 1992

[86] PCT No.: PCT/US92/04255

§ 371 Date: Oct. 21, 1993

§ 102(e) Date: Oct. 21, 1993

[87] PCT Pub. No.: WO92/20377

PCT Pub. Date: Nov. 26, 1992

Related U.S. Application Data

[63] Continuation-in-part of Ser. No. 703,440, May 20, 1991, abandoned, which is a continuation-in-part of Ser. No. 592,712, Oct. 4, 1990, abandoned, which is a continuation-in-part of Ser. No. 482,625, Feb. 21, 1990, abandoned, which is a continuation-in-part of Ser. No. 474,741, Feb. 8, 1990, abandoned, and Ser. No. 204,808, Jun. 9, 1988, abandoned.

[51] Int. Cl.$^6$ .......................................... A61L 15/16
[52] U.S. Cl. .................. 424/447; 424/449; 514/946; 514/947
[58] Field of Search ................... 424/449, 447; 514/946, 947

[56] References Cited

U.S. PATENT DOCUMENTS

| | | | |
|---|---|---|---|
| 3,472,931 | 10/1969 | Stoughton | 424/180 |
| 3,527,864 | 9/1970 | MacMillan et al. | 424/177 |
| 3,598,122 | 8/1971 | Zaffaroni | 128/268 |
| 3,598,123 | 8/1971 | Zaffaroni | 128/268 |
| 3,896,238 | 7/1975 | Smith | 424/358 |
| 3,903,256 | 9/1975 | MacMillan et al. | 424/59 |
| 3,952,099 | 4/1976 | Smith | 424/227 |
| 4,046,886 | 9/1977 | Smith | 424/227 |
| 4,130,643 | 12/1978 | Smith | 424/238 |
| 4,130,667 | 12/1978 | SDmith | 424/361 |
| 4,144,317 | 3/1979 | Higuchi et al. | 424/21 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,568,343 | 2/1986 | Leeper et al. | 604/896 |
| 4,746,515 | 5/1988 | Cheng et al. | 424/449 |
| 4,788,062 | 11/1988 | Gale et al. | 424/449 |
| 4,863,738 | 9/1989 | Taskovich | 424/449 |
| 4,863,970 | 9/1989 | Patel et al. | 514/784 |

FOREIGN PATENT DOCUMENTS

| | | |
|---|---|---|
| 0023349 | 2/1981 | European Pat. Off. . |
| 0103911 | 3/1984 | European Pat. Off. . |
| 0267617 | 5/1988 | European Pat. Off. . |
| 0305026 | 3/1989 | European Pat. Off. . |
| 1001949 | 8/1965 | Germany . |
| 9207590 | 5/1992 | WIPO . |

OTHER PUBLICATIONS

Idson,Percutaneous Absorption, J. Pharm. Sci. (1975) 64:901–924.

Chemical Abstracts, vol. 112, No. 20, (14 May 1990), Abstract No. 185809T.

*Primary Examiner*—D. Gabrielle Phelan
*Attorney, Agent, or Firm*—Michael J. Rafa; Felissa H. Cagan; Steven F. Stone

[57] ABSTRACT

The present invention provides compositions and systems for the transdermal administration of a drug together with glycerol monolinoleate as a permeation enhancer. An example of a delivery system of the invention is a system (20) having a drug reservoir (22) containing together a drug to be delivered and glycerol monolinoleate permeation enhancer. Reservoir is sandwiched between a backing layer (24) and an in-line contact adhesive layer (28).

13 Claims, 1 Drawing Sheet

SKIN PERMEATION ENHANCER COMPOSITIONS USING GLYCEROL MONOLINOLEATE

This application is a 371 of PCT/US92/04255, filed May 20, 1992, which is a continuation-in-part of Ser. No. 07/703,440, filed May 20, 1991, now abandoned, which is a continuation-in-part of Ser. No. 07/592,712, filed Oct. 4, 1990, now abandoned, which is a continuation-in-part of Ser. No. 07/482,625 filed Feb. 21, 1990, now abandoned, which is a continuation-in-part of Ser. No. 07/474,741, filed Feb. 8, 1990, now abandoned, and a continuation-in-part of Ser. No. 07/204,808, filed Jun. 9, 1988, now abandoned, which applications are assigned to ALZA Corporation and benefit is claimed of their filing dates.

FIELD OF THE INVENTION

This invention relates to the transdermal delivery of drugs or other biologically active agents and more particularly to methods and compositions for enhancing the percutaneous absorption of drugs or other agents when incorporated in transdermal drug delivery systems or devices.

BACKGROUND OF THE INVENTION

The transdermal route of parenteral delivery of drugs provides many advantages, and transdermal systems for delivering a wide variety of drugs or other beneficial agents are described in U.S. Pat. Nos. 3,598,122, 3,598,123, 4,379,454, 4,286,592, 4,314,557 and 4,568,343, for example, all of which are incorporated herein by reference. In many cases, drugs which would appear to be ideal candidates for transdermal delivery are found to have such low permeability through intact skin that they cannot be delivered in therapeutically effective amounts from reasonably sized devices.

The terms "therapeutically effective rate" and "therapeutically effective amount", as used herein, refer to a rate or an amount of drug or other agent which provides a therapeutic effect or result.

The term "reasonable size", as used herein, refers to a device of a size with a base surface area (that area in contact with the skin site) that is from about 1 cm$^2$ to about 50 cm$^2$, preferably from about 5 cm$^2$ to about 25 cm$^2$. While devices of as large as 200 cm$^2$ can be considered to be of "conventional" size, such large sizes are not generally acceptable to people, as a practical matter.

In an effort to increase skin permeability so that drugs can be delivered in therapeutically effective amounts, it has been proposed to pretreat the skin with various chemicals or to concurrently deliver the drug in the presence of a permeation enhancer. Various materials have been suggested for this purpose as described in U.S. Pat. Nos. 4,299,826, 4,343,798, 4,046,886, 4,130,643, 4,405,616, 4,335,115, 4,130,667, 3,903,256, 4,379,454, 3,527,864, 3,952,099, 3,896,238, 3,472,931, 4,788,062, 4,746,515, 4,863,738 and 4,863,970; British Pat. No. 1,011,949; and Idson, "Percutaneous Absorption," *J. Pharm. Sci.* (1975) 64:901–924.

It is often difficult to predict which compounds will work as permeation enhancers and which permeation enhancers will work for particular drugs. In systemic drug delivery applications, a compound that enhances the permeability of one drug or a family of drugs may not necessarily enhance the permeability of another drug or family of drugs. Therefore, the usefulness of a particular compound as a permeation enhancer must be analyzed carefully.

DISCLOSURE OF THE INVENTION

According to the present invention, it has been discovered that glycerol monolinoleate (GMLO) is effective in enhancing the permeation of drugs through body surfaces and membranes generally, and through skin in particular. Importantly, glycerol monolinoleate is able to enhance the permeability of these drugs such that they can be delivered at therapeutically effective rates with reasonably sized transdermal delivery devices.

Accordingly, the present invention provides a composition of matter for application to a body surface or membrane to deliver at least one drug, in a therapeutically effective amount, by permeation through the body surface or membrane comprising a least one drug and a permeation-enhancing amount of glycerol monolinoleate. The invention further provides a method for the transdermal coadministration of a therapeutically effective amount of a drug together with a skin permeation-enhancing amount of glycerol monolinoleate.

The system of the invention is a transdermal drug delivery device comprising a matrix adapted to be placed in drug- and permeation enhancer-transmitting relation with the skin or mucosa site. The matrix contains sufficient amounts of glycerol monolinoleate and of a drug to continuously coadminister to the skin for a predetermined period of time the drug and the permeation enhancer to provide a therapeutic effect. The device is of a reasonable size useful for the application of the drug and the enhancer to a human body.

The invention is further directed to a composition of matter which optionally includes, in addition to the drug and GMLO, one or more additional permeation enhancing compounds and to a method for the transdermal administration of such a composition.

DETAILED DISCLOSURE OF THE INVENTION

Figure 1:
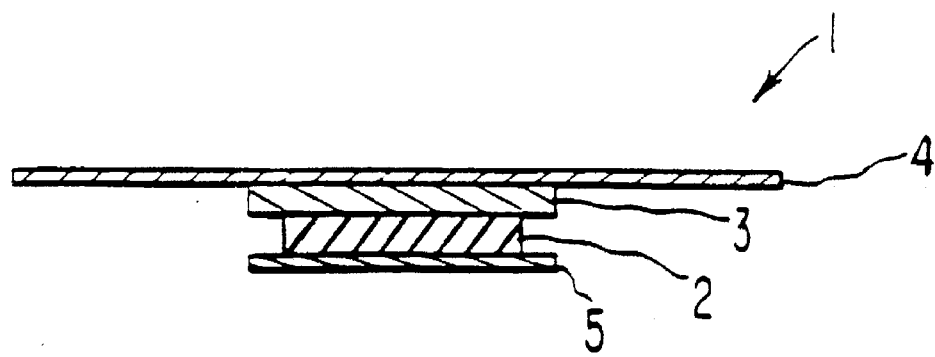
FIG. 1 is a cross-sectional view of one embodiment of a transdermal therapeutic drug delivery device which may be used in accordance with the present invention.

It has now been found that glycerol monolinoleate can be used to effectively enhance the permeability of select drugs through body surfaces and particularly through the skin. Specifically, it has been found that GMLO enhances the permeability such that therapeutically effective amounts of a drug can be delivered from reasonably sized devices at therapeutically effective rates.

It is believed that this invention has utility in connection with the delivery of drugs within the broad class normally delivered through body surfaces and membranes, including skin. As used herein, the expressions "drug" and "agent" are used interchangeably and are intended to have their broadest interpretation as to any therapeutically active substance which is delivered to a living organism to produce a desired, usually beneficial, effect. In as general, this includes therapeutic agents in all of the major therapeutic areas, including, but not limited to, anti-infectives such as antibiotics and antiviral agents, analgesics and analgesic combinations, anorexics, antiarthritics, antiasthmatic agents, anticonvulsants, antidepressants, antidiabetic agents, antidiarrheals, antihistamines, steroidal anti-inflammatory agents, nonsteroidal anti-inflammatory agents, anti-migraine preparations, anti-motion sickness preparations, antinauseants, antineoplastics, antiparkinsonism drugs, antipruritics, antipsychotics, antipyretics, antispasmodics including gastrointestinal and urinary, anticholinergics, sympathomimetrics, xanthine derivatives, cardiovascular preparations including calcium channel blockers, beta-blockers, anti-arrhythmics, antihypertensives, diuretics, vasodilators including general, coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

The utility of GMLO as a permeation enhancer for several dissimilar drugs within the above classes has been demonstrated.

Representative drugs which may be delivered according to the present invention include, by way of illustration but are not limited to, tetracaine, lidocaine, ketoprofen, piroxicam, propranolol, indomethacin, naproxen, nisoldipine, nifedipine, nicardipine, nitrendipine, diclofenac, scopolamine, isosorbide dinitrate, nitroglycerin, estradiol, clonidine, cortisone, theophylline, phenylephrine, terbutaline, ephedrine, narcodine, quinidine, estradiol diacetate, pilocarpine, furosemide, tetracycline, insulin, chlorpheniramine, sulfathiazides, morphinone, morphine, dihydrocodeine, dihydromorphine, oxycodone, hydrocodone, codeine, norcodeine, hydromorphine, normorphine, norlevorphanol, dihydrothebaine, ouabain, bromocriptine, haloperidol, guanabenz, salbutamol, oxprenolol, dibucaine, verapamil, prazosin, doxazosin, diltiazem, atenolol, nadolol, pindolol, timolol, indomethacin, phenylbutazone, benzydamine, and flufenamic acid.

Steroid drugs which may be delivered according to the present invention include, but are not limited to, estrogens and estrogen esters, such as the natural 17β-estradiol (or, estradiol) and estrone and the semi-synthetic estrogen derivatives such as the esters of natural estrogen, such as estradiol-17β-enanthate, estradiol-17β-valerate, estradiol-3-benzoate, estradiol-17β-undecenoate, estradiol-16,17-hemisuccinate or estradiol-17β-cypionate, and the 17-alkylated estrogens, such as ethinyl estradiol, ethinyl estradiol-3-isopropylsulphonate, quinestrol, mestranol or methyl estradiol; progestogens and progestogen esters, such as progesterone, levonorgestrel, norethisterone, gestodene and ST-1435; androgens such as testosterone; and adrenal corticoids and adrenal corticoid esters such as hydrocortisone.

Administration of the drug according to the invention comprises administering the drug at a therapeutically effective rate to an area of a body surface or membrane and simultaneously administering glycerol monolinoleate to the area of the body surface or membrane at rates which are sufficient to substantially increase the permeability of the area to the drug formulation.

According to the invention, GMLO and the drug to be delivered are placed in drug- and GMLO-transmitting relationship to the appropriate body surface, preferably in a carrier therefor, and maintained in place for the desired period of time. The drug and GMLO are typically dispersed within a physiologically compatible matrix or carrier which may be applied directly to the body surface or skin as an ointment, gel, cream, suppository or sublingual or buccal tablet, for example, but are more preferably administered from a transdermal therapeutic delivery device as more fully described below.

GMLO is a known compound for use as an ingredient in cosmetics or as a food additive. Its use as a permeation enhancer for enhancing the permeation of a drug or other agent through the skin has not been previously known. GMLO has a low toxicity and is colorless and odorless. Additionally, it does not produce irritation, even on prolonged exposure and under occlusion, and it does not sensitize the skin on repeated exposure. Further, it is capable of enhancing drug flux for improved delivery of drugs without producing objectionable skin sensations, such as burning or tingling.

GMLO has a permeation-enhancing effect on the transport of drugs through body surface tissues generally, in addition to the skin. However, because skin is one of the most effective body barriers to the permeation of foreign substances, the effect of GMLO on skin permeation makes it extremely useful in transdermal delivery. The following description of embodiments of the invention is therefore directed primarily to improving systemic delivery of these drugs.

It may be desirable in certain instances or with certain drugs to include one or two permeation enhancers in addition to the GMLO. Thus, in certain embodiments of the present invention, a second permeation enhancer is included together with the drug and GMLO. This second enhancer may be selected from those compounds that have a permeation-enhancing effect with the drug and are compatible with the drug and with GMLO. In a presently preferred embodiment, the second permeation enhancer is methyl laurate and/or a lower $C_{1-4}$ alkanol, preferably ethanol. While it is known in the art to combine permeation enhancers, this invention utilizes a novel combination of is ethanol and/or GMLO. The combined effect produces a significant and surprising improvement over use of either GMLO or ethanol alone.

Figure 3:
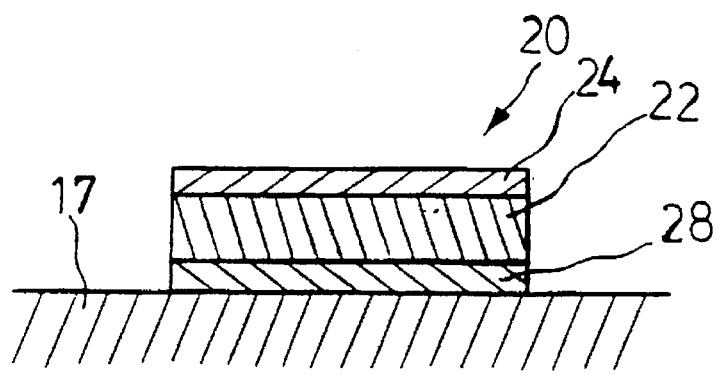
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a drug- and glycerol monolinoleate-containing reservoir ("drug reservoir") 2 which is preferably in the form of a matrix containing the drug and the enhancer dispersed therein. In those embodiments which include a second permeation enhancer, drug reservoir 2 also includes this second enhancer. An impermeable backing layer 3 is provided adjacent one surface of drug reservoir 2. Adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. Impermeable backing layer 3 is preferably slightly larger than drug reservoir 2, and in this manner prevents the materials in drug reservoir 2 from adversely interacting with the adhesive in overlay 4. A strippable or removable liner 5 is also provided with device 1 and is removed just prior to application of device 1 to the skin.

Figure 2:
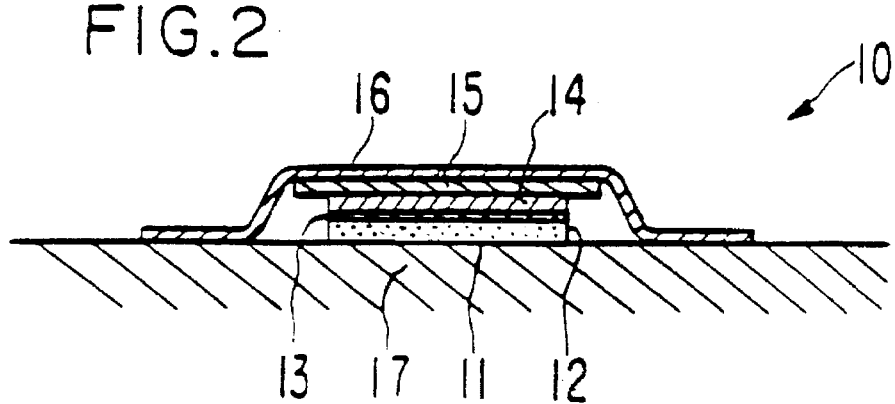
FIG. 2 is a cross-sectional view of another embodiment of a transdermal therapeutic drug delivery device which may be-used in accordance with the present invention.

FIG. 2 illustrates another embodiment of the invention, device 10, shown in place upon the skin 17. In this embodiment, the transdermal therapeutic delivery device 10 comprises a multilaminate drug formulation/enhancer reservoir 11 having at least two zones 12 and 14. Zone 12 consists of a drug reservoir substantially as described with respect to FIG. 1. Zone 14 comprises a GMLO reservoir which is preferably made from substantially the same matrix as is used to form zone 12. Zone 14 comprises GMLO dispersed throughout and is substantially free of any undissolved drug. A second permeation enhancer may optionally be included in zone 14 as well. A rate-controlling membrane 13 for controlling the release rate of the GMLO and, optionally, any second enhancer from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane may be fabricated from permeable, semipermeable or microporous materials which are known in the art to control the rate of agents into and out of delivery devices and having a permeability to the permeation enhancer lower than that of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of the reservoir 11. This functions to reduce the amount of drug in the device while maintaining an adequate supply of GMLO permeation enhancer.

Superimposed over the drug formulation/enhancer-reservoir 11 of device 10 is an impermeable backing 15 and an adhesive overlay 16 as described above with respect to FIG. 1. In addition, a strippable liner (not shown) would preferably be provided on the device prior to use as described with respect to FIG. I and removed prior to application of the device 10 to the skin 17.

In the embodiments of FIGS. 1 and 2, the carrier or matrix material has sufficient viscosity to maintain its shape without oozing or flowing. If, however, the matrix or carrier is a lows viscosity flowable material, the composition can be fully enclosed in a pouch or pocket formed between the impermeable backing and a permeable or microporous skin-contacting membrane, as known to the art from U.S. Pat. No. 4,379,454 (noted above), for example.

An example of a presently preferred transdermal delivery device is illustrated in FIG. 3. In FIG. 3, transdermal delivery device 20 comprises a drug reservoir 22 containing together the drug and the GMLO permeation enhancer. Optionally, a second permeation enhancer may also be included in drug reservoir 22. Reservoir 22 is preferably in the form of a matrix containing the drug and the enhancer dispersed therein. Reservoir 22 is sandwiched between a backing layer 24, which is impermeable to both the drug and the GMLO, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the drug or, in particular, the GMLO permeation enhancer. The adhesive layer 28 may optionally contain enhancer and/or drug. A strippable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-side of the rate-controlling membrane.

Various materials suited for the fabrication of the various layers of the transdermal devices of FIGS. 1, 2 or 3 are known in the art or are disclosed in the aforementioned transdermal device patents previously incorporated herein by reference.

The matrix making up the drug/GMLO permeation enhancer reservoir can be a gel or a polymer. Suitable materials should be compatible with the drug and GMLO and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to a drug and GMLO, which are essential to the invention, the matrix may also contain stabilizers, dyes, pigments, inert fillers, tackifiers, excipients and other conventional components of transdermal delivery devices as are known in the art.

The amounts of the drug that are present in the therapeutic device, and that are required to achieve a therapeutic effect, depend on many factors, such as the minimum necessary dosage of the particular drug; the permeability of the matrix, of the adhesive layer and of the rate-controlling membrane, if present; and the period of time for which the device will be fixed to the skin. There is, in fact, no upper limit to the maximum amounts of drug present in the device. The minimum amount of each drug is determined by the requirement that sufficient quantities of drug must be present in the device to maintain the desired rate of release over the given period of application.

The drug is generally dispersed through the matrix at a concentration in excess of saturation, i.e. at unit activity. The amount of excess is determined by the intended useful life of the system. However, the drug may be present at initial levels below saturation without departing from this invention. For certain particular steroidal drugs, such as certain synthetic estrogens, the concentration in the matrix is generally in an amount-below saturation, as the flux of the estrogen through human epidermis has been found to be proportional to the concentration of estrogen in the drug reservoir.

The glycerol monolinoleate is dispersed throughout the matrix, preferably at a concentration sufficient to provide permeation-enhancing concentrations of enhancer in the reservoir throughout the anticipated administration period.

In certain embodiments of the invention, a second permeation enhancer, such as ethanol and/or methyllaurate, is also dispersed throughout the matrix, preferably at a concentration sufficient to provide permeation-enhancing concentrations of enhancer in the drug reservoir throughout the anticipated administration period.

In the present invention, the drug is delivered through the skin or other body surface at a therapeutically effective rate (that is, a rate that provides an effective therapeutic result) and the GMLO is delivered at a permeation-enhancing rate (that is, a rate that provides increased permeability of the application site to the drug) for a predetermined time period.

A preferred embodiment of the present invention is a monolith such as that illustrated in FIG. 3 (either with or without a rate-controlling membrane) wherein reservoir 22 comprises, by weight, 50–90% polymer (preferably EVA), 0.01–20% drug, and 1–70% GMLO. The in-line adhesive layer 28 contains an adhesive which is compatible with the permeation enhancer. In another preferred embodiment of the invention, a monolith such as that in FIG. 3 includes reservoir 22 comprising, by weight, 30–90% polymer (preferably EVA), 0.01–20% drug, 1–70% GMLO and 1–45% ethanol and/or 1–45% methyl laurate.

The devices of this invention can be designed to effectively deliver a drug for an extended time period of up to 7 days or longer. Seven days is generally the maximum time limit for application of a single device because the skin site is adversely affected by a period of occlusion greater than 7 days. Where it is desired to have drug delivery for greater than 7 days (such as, for example, when a hormone is being applied for a contraceptive effect), when one device has been in place on the skin for its effective time period, it is replaced with a fresh device, preferably on a different skin site.

The transdermal therapeutic devices of the present invention are prepared in a manner known in the art, such as by those procedures, for example, described in the transdermal device patents listed previously herein.

The following examples are offered to illustrate the practice of the present invention and are not intended to limit the invention in any manner.

BEST MODE OF THE INVENTION

The devices used in the following Examples 1–5 were prepared as follows:

The drug to be tested, at the appropriate concentration, the GMLO, at the appropriate concentration, and EVA 40% VA ("EVA 40") were dissolved in methylene chloride. The solution was poured onto an FCD/polyester release liner to evaporate. The dried material was then pressed to 4–5 mil (ca. 0.1 mm) thickness between two sheets of FCD/polyester release liner at 75° C. The resulting film was heat-laminated to an impermeable backing (Medpar® or Scotchpak®, for example), and discs or squares were punched or die-cut from the laminate.

Where an in-line adhesive was included as a part of the device, the drug matrix/impermeable backing laminate was laminated to an adhesive. Before testing, each final laminate with adhesive was equilibrated for at least 5 days to allow the enhancer and the drug to partition into the contact adhesive. The edges of the devices with in-line adhesive were masked with polyester tape so that the drug reservoir edges were not exposed to the epidermis or solutions when they were tested.

EXAMPLE 1

The in vitro transdermal flux of gestodene together with GMLO, with or without an in-line adhesive, was determined for epidermis from a human cadaver. A control device containing gestodene but no GMLO enhancer was also tested.

The epidermis was separated from the dermis of the skin donor after immersion in 60° C. water for 75 seconds. Discs (of a size larger than the device to be tested) were cut from the epidermis, and the discs were kept at 4° C. in a hydrated state until they were used.

For each device tested, the release liner of the device was removed and the drug-releasing surface was placed against the stratum corneum side of a disc of epidermis which had been blotted dry just prior to use. The excess epidermis was wrapped around the device so that none of the device edge was exposed to the receptor solution. The device covered with epidermis was attached to the flat side of the Teflon holder of a release rate rod using nylon netting and nickel wire. The rods were reciprocated in a fixed volume of receptor solution (distilled water). The entire receptor solution was changed at each sampling time. The temperature of the receptor solution in the water bath was maintained at 35° C.

A summary of the results is given in Table I below.

TABLE I

| Average Transdermal Gestodene Flux, 7–96 hrs ($\mu g/cm^2$-hr) | | | |
|---|---|---|---|
| Wt % GMLO | 30 | 30 | 0 |
| Wt % Gestodene | 2.0 | 8.0 | 6.0 |
| Without Adhesive | 0.37 | 0.43 | 0.08 |
| With Adhesive | 0.44 | 0.39 | — |

The GMLO used was Myverol® 1892K (Eastman Chemical Products; glycerol monolinoleate content of 68% and a total monoesters content of 90%). The adhesive was 3M acrylate transfer adhesive MSP 32589 (an acrylate adhesive with 2–5% acid functionality).

EXAMPLE 2

The in vitro transdermal flux of estradiol, without an in-line adhesive, was determined for epidermis from two human cadavers, following the procedures of Example 1. The devices contained 2 wt % estradiol and 30 wt % Myverol 1892K GMLO in an EVA 40 matrix. The resulting average flux over 74 hours was 0.15 $\mu g/cm^2$- hr (average of the two donors), in comparison to a control without GMLO which had an average flux of 0.02 $\mu g/cm^2$-hr.

EXAMPLE 3

The in vitro transdermal flux of atenolol, from devices as in FIG. 3 both with and without an in-line adhesive, was determined for epidermis from three human cadavers, following the procedures of Example 1. The devices contained 20 wt % atenolol base and 30 wt % Myverol 1892K GMLO in an EVA 40 matrix. The adhesive on those devices with adhesive was polyisobutylene-LMMS/polyvinylpyrrolidone L10 (80/20). Control devices were also tested for comparison. The resulting average flux over 53 hours is presented in Table II below.

TABLE II

| AVERAGE TRANSDERMAL ATENOLOL FLUX ($\mu g/cm^2$-hr) | | |
|---|---|---|
| Permeation Enhancer | Without Adhesive | With Adhesive |
| GMLO | 14.0 | 10.0 |
| None (Control) | 0.65 | 0.51 |

EXAMPLE 4

The in vitro transdermal flux of progesterone, from a device as in FIG. 3 without an in-line adhesive, was determined for epidermis from one human cadaver (n=2), following the procedures of Example 1. The devices contained 20 wt % progesterone and 45 wt % Myverol 1892K GMLO in an EVA 40 matrix. The resulting average flux for 24–48 hours was 2.5 $\mu g/cm^2$-hr, whereas the average flux of the control (20 wt % progesterone in EVA 40, no GMLO) was <0.01 $\mu g/cm^2$-hr.

EXAMPLE 5

The in vitro transdermal flux of oxybutynin, from a device as in FIG. 3 without an in-line adhesive, was determined for epidermis from two human cadavers, following the procedures of Example 1. The devices contained 30 wt % oxybutynin base and 25 wt % Myverol 1892K GMLO in an EVA 40 matrix. The resulting average flux over 77 hours was 3.8 μg/cm²-hr, whereas the average flux of the control was 1.0 μg/cm²-hr. The matrix was subsaturated with the permeation enhancer, whose saturation concentration is about 45 wt %. The flux would be further enhanced by including a larger percentage of GMLO in the matrix.

EXAMPLE 6

The transdermal permeation through human cadaver epidermis of a composition of the present invention containing diclofenac (as the diethylammonium salt) was determined and was compared to a prior art diclofenac-containing topical gel, Voltarene® Emulgel® (1.16% diclofenac diethylammonium salt; Ciba-Geigy). The 1.16% ammonium salt was equivalent to 1.0% doclofenac sodium salt or 0.93% diclofenac acid.

The composition of the invention (composition A) comprised 29.04 wt % Myverol 1892K GMLO, 43.59 wt % ethanol, 24.21 wt % water (as the carrier), 1.16 wt % diclofenac diethylammonium salt, and 2.0 wt % hydroxypropylcellulose (HPC; gelling agent). In preparing the composition, first, the GMLO, ethanol and the water were mixed together, after which the HPC was added, followed by addition of the drug compound.

Composition A and the prior art compound were each placed on human cadaver epidermis and the amounts of drug permeated across the epidermis at 35° C. in standard diffusion cells was measured over 48 hours. In one test, the donor loading was 10 mg/1.13cm² and in a second test, the donor loading was 50 mg/1.13 cm² of skin area. All applications were non-occluded. The total diclofenac which permeated through 1.0 cm² of epidermis into a receptor solution was determined over 48 hours and is presented in Table III below.

TABLE III

| Composition | Total Permeated (mg/cm²/48 hr) | |
|---|---|---|
| | 10 mg/1.13 cm² | 50 mg/1.13 cm² |
| A | 0.20 | 0.65 |
| Voltarene Emulgel | 0.16 | 0.43 |

EXAMPLE 7

Following the procedures of Example 6, the transdermal permeation through human cadaver epidermis of two compositions of the present invention containing hydrocortisone was determined and was is compared to a prior art hydrocortisone-containing topical gel, Dermolate® (0.5% hydrocortisone; Schering Corporation).

The first composition of the invention (composition A) comprised 29.20 wt % Myverol 1892K GMLO, 43.88 wt % ethanol, 24.42 wt % water (as the carrier), 0.05 wt % hydrocortisone, and 2.0 wt % hydroxypropylcellulose (HPC; gelling agent). Composition B of the invention comprised 61.44 wt % Myverol 1892K, 13.89 wt % ethanol, 23.97 wt % water, and 0.50 wt % hydrocortisone. Composition B formed a kind of ointment and did not need to be gelled.

Following procedures as described in Example 6, the two compositions and Dermolate were tested for in vitro drug permeation through human cadaver skin, at 35° C. In one test, the donor loading was 10 mg/1.13 cm² and in a second test, the donor loading was 50 mg/1.13 cm² of skin area. All applications were non-occluded. The total hydrocortisone which permeated through 1.0 cm² of epidermis into a receptor solution was determined over 48 hours and is presented in Table IV below.

TABLE IV

| Composition | Total Permeated (mg/cm²/48 hr) | |
|---|---|---|
| | 10 mg/1.13 cm² | 50 mg/1.13 cm² |
| A | 0.13 | 0.16 |
| B | 0.21 | 0.42 |
| Dermolate | 0.005 | 0.02 |

EXAMPLE 8

Following the procedures of Example 6, the transdermal permeation through human cadaver epidermis of a composition of the present invention containing ketoprofen was determined and was compared to a prior art ketoprofen-containing topical ointment, Profenid® gel (2.5% ketoprofen; Specia Rhone Poulenc).

The vehicle of the invention comprised 43.0 wt % ethanol (95%, USP), 28.7 wt % Myverol 1892K GMLO and 23.9 wt % water. Two wt % of hydroxypropylcellulose was added to the vehicle as a gelling agent, after which 2.5 wt % of ketoprofen was added to the vehicle. Following procedures as earlier described, the vehicle and Profenid were tested for drug permeation rate through human cadaver skin by using standard two-compartment horizontal permeation cells, at 35° C. The total ketoprofen which permeated through 1.0 cm² of epidermis over the first 24 hours was 0.45 mg/cm², whereas the total of Profenid permeated was 0.23 mg/cm².

EXAMPLE 9

Following the procedures of Example 6, the transdermal permeation through human cadaver epidermis of two [?] compositions of the present invention containing piroxicam was determined and was compared to a prior art piroxicam-containing topical ointment, Feldene® gel (0.5% piroxicam; Pfizer).

The vehicle composition of the invention was comprised of 43.9 wt % ethanol (95%, USP), 29.3 wt % Myverol 1892K GMLO and 24.4 wt % water. Piroxicam (0.52 wt % sodium piroxicam) and 2.0 wt % of hydroxypropylcellulose (as a gelling agent) were added to the vehicle. Following procedures as described above, the in vitro permeation of piroxicam through cadaver skin from the vehicle and from Feldene, at 35° C., were determined. The total piroxicam which permeated per 1.0 cm² of epidermis into an aqueous receptor solution over the first 24 hours was 0.6 μg/cm², and the total Feldene permeated was <0.02 μg/cm².

EXAMPLE 10

The in vivo transdermal permeation through human skin of testosterone utilizing a composition of the present invention was determined as follows.

The composition comprised 26.4 wt % Myverol 1892K GMLO, 37.0 wt % ethanol, 24.6 wt % water, 10.0 wt % testosterone and 2.0 wt % HPC. In preparing the composition, first, the GMLO, ethanol and water were mixed together, after which the HPC was added, followed by addition of the testosterone.

The resulting gel was placed into a 10 cm² cup, and three of these systems were applied onto the chest of a healthy male and were taped in place. The systems were maintained on the chest for 8 hr. Blood was drawn prior to placement of the systems (to obtain a baseline) and then at 2 hr, 4 hr and 8 hr after placement, and the amount of testosterone and of dihydrotestosterone in the plasma was analyzed. At 0 hr, the testosterone level in the plasma was 429 ng/dL; after placement of the testosterone systems, the amount of testosterone rose significantly, to 725 ng/dL at 2 hr, to 958 ng/dL at 4 hr, and to 783 ng/dL at 8 hr. During this period, the plasma level of dihydrotestosterone did not change significantly, ranging between 56 and 96 ng/dL.

EXAMPLE 11

Following the procedures of Example 10, a composition containing testosterone, according to the present invention, was prepared having the following composition: 35.4 wt % Myverol 1892K GMLO, 35.4 wt % methyl laurate, 17.7 wt % ethanol, 10.0 wt % testosterone, and 2.0 wt % HPC.

This composition was tested for in vivo delivery of testosterone, following the procedures of Example 10. The composition gave increased blood plasma levels of testosterone over 8 hr—370 ng/dL at 0 hr, 725 ng/dL at 2 hr, 901 ng/dL at 4 hr, and 665 ng/dL at 8 hr. The dihydrotestosterone plasma level ranged between 54 and 93 ng/dL during this period.

This invention has been described in detail with particular reference to certain preferred embodiments thereof, but it will be understood that variations and modifications can be effected within the spirit and scope of the invention.

What is claimed is:

1. A non-aqueous composition of matter for the transdermal application to a body surface or membrane of at least one drug, at a therapeutically effective rate, the composition comprising, in combination, a therapeutically effective amount of at least one drug and a permeation-enhancing amount of glycerol monolinoleate.

2. A composition according to claim 1 further comprising a carrier having the drug and glycerol monolinoleate dispersed throughout.

3. A composition according to claim 1 wherein the body surface or membrane is intact skin.

4. A composition according to claim 1 which further comprises ethanol, in a permeation-enhancing amount.

5. A delivery system for the transdermal application to a body surface or membrane of at least one drug, at a therapeutically effective rate, the therapeutic system comprising a non-aqueous composition which comprises a permeation-enhancing amount of glycerol monolinoleate and a therapeutically effective amount of drug in a matrix or carrier.

6. A system according to claim 5 wherein the composition comprises 0.01–20 wt percent drug and 0.01–70 wt percent glycerol monolinoleate.

7. A system according to claim 5 further comprising:

a backing behind the skin distal surface of the composition; and means for maintaining the composition in drug- and glycerol monolinoleate-transmitting relationship to the body surface or membrane.

8. A system according to claim 5 wherein the composition further comprises a permeation-enhancing amount of ethanol.

9. A system according to claim 5 wherein the body surface or membrane is skin.

10. A system according to claim 5, 6 or 7 wherein the matrix comprises ethylene vinyl acetate copolymer having from about 9 to 60% vinyl acetate.

11. A system according to claim 7 wherein the means for maintaining the composition in relation with the skin comprises an in-line adhesive layer on the skin-proximal surface of the reservoir.

12. A delivery system for the transdermal application to a body surface or membrane of at least one drug at a therapeutically effective rate, the therapeutic system comprising a non-aqueous composition which comprises a permeation-enhancing amount of glycerol monolinoleate and ethanol in combination and a therapeutically effective amount of a drug in a matrix or carrier.

13. A system according to claim 12 further comprising;

a backing behind the skin distal surface of the composition; and means for maintaining the composition in drug- and glycerol monolinoleate-transmitting relationship to the body surface or membrane.

* * * * *